US012690849B2

(12) United States Patent
Gu et al.

(10) Patent No.: US 12,690,849 B2
(45) Date of Patent: Jul. 28, 2026

(54) ATRIAL SEPTAL DEFECT OCCLUDER

(71) Applicant: NATIONAL CENTER FOR CARDIOVASCULAR DISEASE AND FUWAI HOSPITAL, Beijing (CN)

(72) Inventors: Yuanrui Gu, Beijing (CN); Chenxi Ouyang, Beijing (CN); Yangxue Sun, Beijing (CN); Yunhong Wang, Beijing (CN); Huichai Li, Beijing (CN); Sishi Liu, Beijing (CN)

( * ) Notice: Subject to any disclaimer, the term of this patent is extended or adjusted under 35 U.S.C. 154(b) by 72 days.

(21) Appl. No.: 18/556,823

(22) PCT Filed: May 10, 2022

(86) PCT No.: PCT/CN2022/091904
§ 371 (c)(1),
(2) Date: Oct. 23, 2023

(87) PCT Pub. No.: WO2023/005334
PCT Pub. Date: Feb. 2, 2023

(65) Prior Publication Data
US 2024/0197307 A1 Jun. 20, 2024

(30) Foreign Application Priority Data
Jul. 26, 2021 (CN) .......................... 202110843440.3

(51) Int. Cl.
*A61B 17/00* (2006.01)
*A61B 17/12* (2006.01)

(52) U.S. Cl.
CPC .... *A61B 17/0057* (2013.01); *A61B 17/12168* (2013.01); *A61B 2017/00575* (2013.01)

(58) Field of Classification Search
CPC ........ A61B 17/12122; A61B 17/12168; A61B 17/12172; A61B 17/0057;
(Continued)

(56) References Cited

U.S. PATENT DOCUMENTS

2017/0224323 A1* 8/2017 Rowe ................. A61B 17/0218
2017/0273790 A1* 9/2017 Vettukattil .......... A61M 27/002
(Continued)

*Primary Examiner* — Wade Miles

(57) ABSTRACT

An atrial septal defect occluder, including: a body (100, 510), including two disk surfaces arranged opposite to each other and provided with a through hole (130) along an axial direction of the body (100, 510); and a blocking assembly, including an openable choke film (200) or elastic body (520), the blocking assembly being in contact with the body (100, 510), wherein when the blocking assembly is in a closed state, the blocking assembly impedes liquid from flowing in the through hole (130), and when the blocking assembly is in an open state, the blocking effect is weakened or even eliminated, thus allowing a minimally invasive interventional device to pass through the occluder by means of the through hole (130). By means of the interaction between the through hole (130) in the body (100, 510) and the blocking assembly of the occluder, the occluder may not only seal an atrial septal defect, but may also achieve the function of allowing a minimally invasive interventional device to pass by means of the through hole (130) when necessary, thus preventing repeated perforation treatments.

1 Claim, 12 Drawing Sheets

(58) Field of Classification Search
CPC ........... A61B 2017/00575; A61B 2017/00592;
A61B 2017/00587; A61B 2017/00606
See application file for complete search history.

(56) References Cited

U.S. PATENT DOCUMENTS

2021/0059650 A1 * 3/2021 Eidenschink ...... A61B 17/0057
2021/0307735 A1 * 10/2021 Russo ................... B21F 45/008

* cited by examiner

130

140

110

120

140

100

200

420

421

520

510

521

500

521

510

520

ATRIAL SEPTAL DEFECT OCCLUDER

CROSS-REFERENCE TO RELATED APPLICATION

This application is a Section 371 National Stage Application of International Application No. PCT/CN2022/091904, filed on May 10, 2022, entitled "ATRIAL SEPTAL DEFECT OCCLUDER", which claims priority to Chinese Application No. CN 202110843440.3, filed on Jul. 26, 2021, incorporated herein by reference in their entirety.

TECHNICAL FIELD

The present disclosure relates to the field of medical devices, and specifically to an atrial septal defect occluder.

BACKGROUND

Atrial septal defect in congenital heart disease is a common type of congenital heart malformation disease. It refers to abnormalities in the occurrence, absorption and fusion of the atrial septum during the embryonic development period, resulting in a residual patent defect between the left and right atria. Since the pressure in the left atrium is higher than that in the right atrium, under the action of pressure, part of the blood in the left atrium is shunted to the right atrium through the atrial septal defect, which increases the burden on the right heart system, causes right ventricular hypertrophy, increases the blood volume of the pulmonary circulation, and eventually possibly causes pulmonary hypertension, arrhythmias, and heart failure.

For the treatment of atrial septal defect, surgical thoracotomy is initially used. Although the surgery is safe and effective in repairing the defect, the thoracotomy is invasive to the patient, has a high incidence of complications, and leaves surgical scars on the body surface. In recent years, minimally invasive interventional treatment methods have gradually entered people's field of vision. Currently, the more commonly used atrial septal defect occluders on the market are mostly made of nickel-titanium alloy wires. The inside of the occluder is filled with flow-blocking (choke) media, it may be sent to the heart defect site through a cardiac catheter to close the atrial septal defect, so as to prevent blood from entering from the left atrium to the right atrium. This occluder causes less damage to blood vessels, is easy to operate, and has a high success rate, making it the preferred device for atrial septal defects.

The inventors found that when pulmonary hypertension leads to right heart failure and the blood in the right atrium needs to be shunted and decompressed, it is necessary to perforate again at other positions of the interatrial septum of the patient's left and right atria to implant an atrial shunt or a minimally invasive interventional device (such as a cardiac catheter, etc.); or when a minimally invasive interventional device needs to enter the left atrium through the interatrial septum between the right atrium and the left atrium for interventional treatment, it also needs to pass through the perforation. Therefore, when a second operation is required, another perforation is needed in the patient's interatrial septum. On the one hand, it increases the complexity of the operation, on the other hand, it also causes secondary damage to the patient and brings great pains to the patient.

SUMMARY

In order to solve the problems in the prior art, there is provided an atrial septal defect occluder in embodiments of the present disclosure.

In a first aspect, there is provided in an embodiment of the present disclosure an atrial septal defect occluder, specifically, including:

a body, comprising two disk surfaces arranged opposite to each other and provided with a through hole along an axial direction of the body; and a blocking assembly, comprising an openable choke film or elastic body, the blocking assembly being in contact with the body, wherein when the blocking assembly is in a closed state, the blocking assembly impedes liquid from flowing in the through hole, and when the blocking assembly is in an open state, a blocking effect is weakened or even eliminated, thus allowing a minimally invasive interventional device to pass through the occluder by means of the through hole.

In conjunction with the first aspect, in a first embodiment of the first aspect of the present disclosure, the two disk surfaces comprise a left heart disk surface and a right heart disk surface, the blocking assembly comprises a choke film disposed on the left heart disk surface, the choke film comprises a fixed end and an open end, the choke film is fixed to the left heart disk surface through the fixed end, and the choke film covers the through hole in the closed state.

In conjunction with the first aspect, in a second embodiment of the first aspect of the present disclosure, the blocking assembly comprises two choke films respectively disposed on the two disk surfaces, each of the choke films comprises a fixed end and an open end, each of the choke films is fixed to one disk surface through the fixed end, and each of the choke films covers the through hole in the closed state.

In conjunction with the first or second embodiment of the first aspect, in a third embodiment of the first aspect of the present disclosure, the body is of a mesh structure, the choke film is woven together with the body through the fixed end, pores are provided in a surface of the choke film, the pores being filled with blocking media.

In conjunction with the third embodiment of the first aspect, in a fourth embodiment of the first aspect of the present disclosure, the body and the choke film are woven from at least one of materials such as nickel-titanium alloy wire, iron wire, aluminum wire or polylactic acid, the blocking media is made from at least one of materials such as polytetrafluoroethylene, polyurethane or polyester.

In conjunction with the second embodiment of the first aspect, in a fifth embodiment of the first aspect of the present disclosure, the two disk surfaces comprise a left heart disk surface and a right heart disk surface, and a pulling wire is provided on the open end of the choke film of the right heart disk surface.

In conjunction with the first aspect, in a sixth embodiment of the first aspect of the present disclosure, the two disk surfaces comprise a left heart disk surface and a right heart disk surface, the blocking assembly comprises a choke film disposed on the left heart disk surface, the choke film is peripherally fixed to the left heart disk surface and covers the through hole, the choke film is provided with an opening, and the opening and the through hole do not overlap in an axial direction of the occlude.

In conjunction with the sixth embodiment of the first aspect, in a seventh embodiment of the first aspect of the present disclosure, the blocking assembly further comprises a choke film disposed on the right heart disk surface, the choke film on the right heart disk surface comprises a fixed end and an open end, the choke film on the right heart disk surface is fixed to the right heart disk surface through the fixed end, and the choke film on the right heart disk surface covers the through hole in the closed state.

In conjunction with the first aspect, in an eighth embodiment of the first aspect of the present disclosure, the blocking assembly comprises an elastic body filled in the through hole, a channel is provided inside the elastic body, and the channel is configured to be sealed by an elasticity of the elastic body.

In conjunction with the eighth embodiment of the first aspect, in a ninth embodiment of the first aspect of the present disclosure, the elastic body is composed of at least one of polyurethane elastic body or polytetrafluoroethylene elastic body.

In conjunction with the eighth or ninth embodiment of the first aspect, in a tenth embodiment of the first aspect of the present disclosure, a developing line is provided in the channel of the elastic body.

According to the technical solutions provided in the embodiments of the present disclosure, by means of the interaction between the through hole in the body and the blocking assembly of the occluder, the occluder may not only seal an atrial septal defect, but may also achieve the function of allowing a minimally invasive interventional device to pass or shunting by means of the through hole when necessary, thus preventing repeated perforation treatments.

It should be understood that the above general description and the following detailed description are only illustrative and explanatory, and do not limit the present disclosure.

BRIEF DESCRIPTION OF THE DRAWINGS

Other features, objects and advantages of the present disclosure will become more apparent through the following detailed description of the non-limiting embodiments in conjunction with the accompanying drawings. The following is a description of the accompanying drawings.

DETAILED DESCRIPTION OF EMBODIMENTS

Figure 1A:
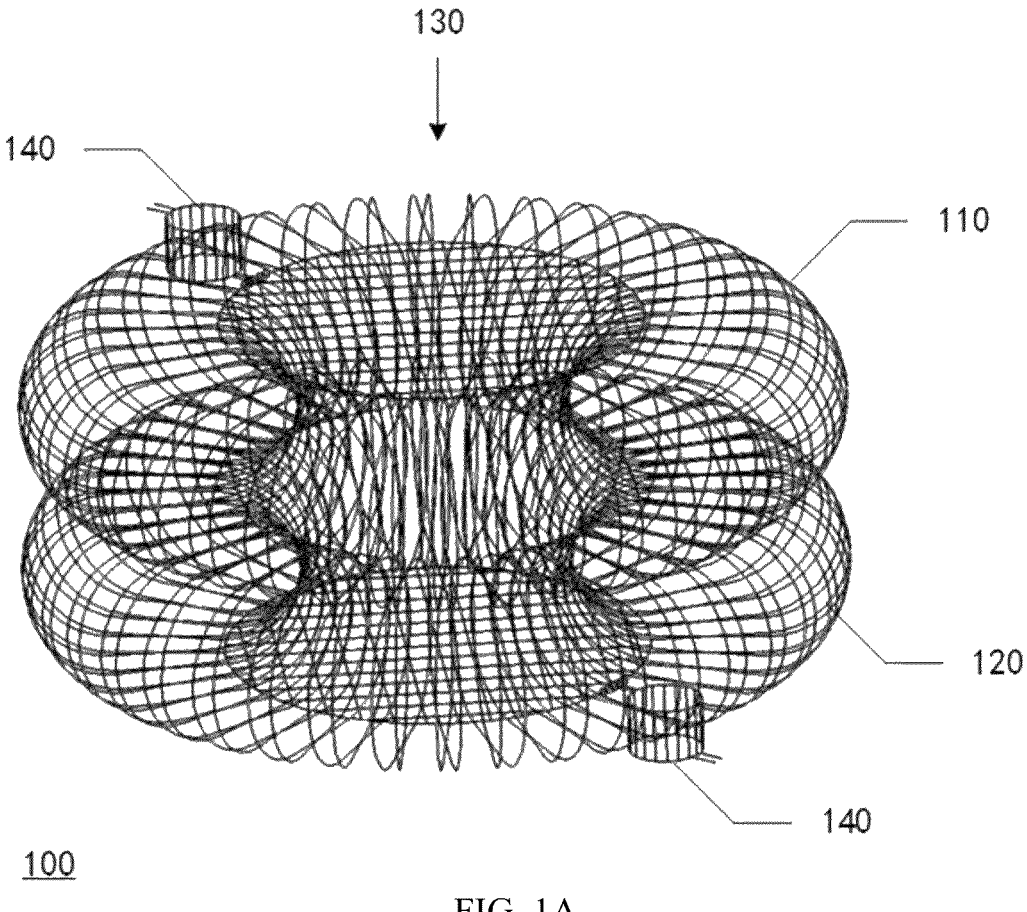
FIGS. 1A and 1B are schematic views of a body of an atrial septal defect occluder according to an embodiment of the present disclosure.

Hereinafter, exemplary embodiments of the present disclosure will be described in detail with reference to the accompanying drawings so that they would be easily implemented by those skilled in the art. Furthermore, for clarity, parts irrelevant to describing the exemplary embodiments are omitted in the drawings.

In the present disclosure, it should be understood that terms such as "comprising" or "having" are intended to indicate that the presence of features, numbers, steps, acts, components, portions, or combinations thereof disclosed in this specification does not exclude the possibility that one or more other features, numbers, steps, acts, components, portions, or combinations thereof exist or are added.

It should also be noted that the embodiments and features in the embodiments of the present disclosure can be combined with each other as long as there is no conflict. The present disclosure will be described in detail below in conjunction with the embodiments with reference to the accompanying drawings.

In an embodiment of the present disclosure, there is provided an atrial septal defect occluder, including:

a body, comprising two disk surfaces arranged opposite to each other and provided with a through hole along an axial direction of the body; and a blocking assembly, comprising an openable choke film (flow blocking film) or elastic body, wherein when the blocking assembly is in a closed state, the blocking assembly impedes liquid from flowing in the through hole, and when the blocking assembly is in an open state, a blocking effect is weakened or even eliminated, thus allowing a minimally invasive interventional device to pass through the occluder by means of the through hole.

According to embodiments of the present disclosure, the blocking assembly is generally at least partially in contact with the body to perform a blocking effect.

According to the technical solutions provided in the embodiments of the present disclosure, by means of the interaction between the through hole in the body and the blocking assembly of the occluder, the occluder may not only seal an atrial septal defect, but may also achieve the function of allowing a minimally invasive interventional device to pass or shunting by means of the through hole when necessary, thus preventing repeated perforation treatments.

Figure 1B:
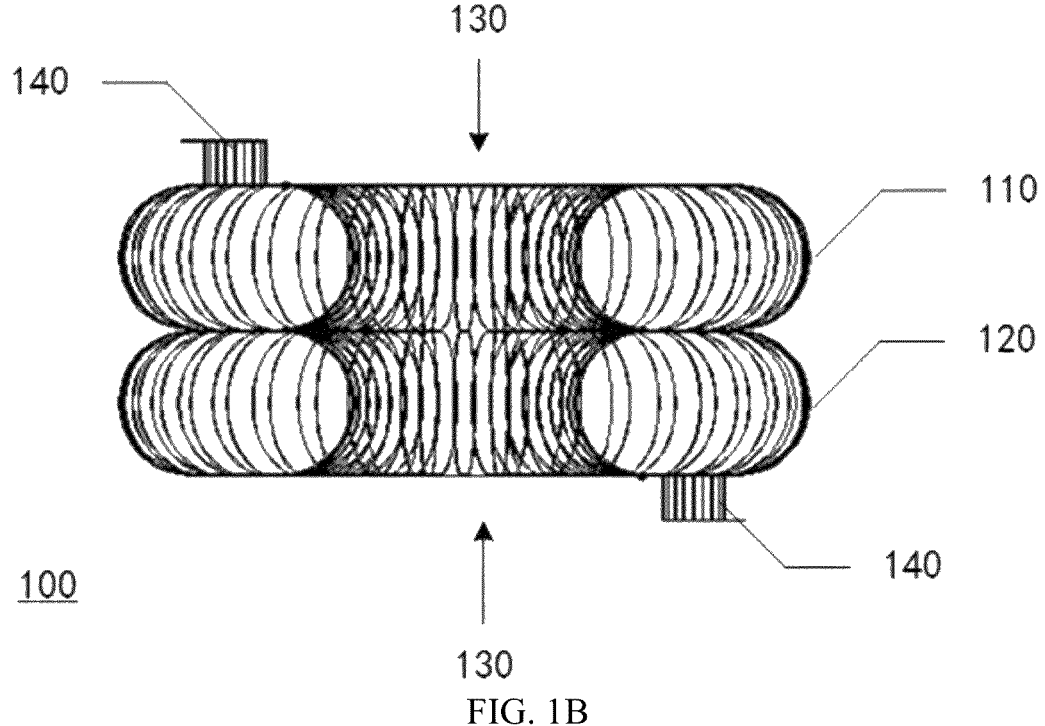

FIGS. 1A and 1B are schematic views of a body 100 of an atrial septal defect occluder according to an embodiment of the present disclosure. Among them, FIG. 1A is a three-dimensional perspective view, and FIG. 1B is a side view.

According to embodiments of the present disclosure, the body 100 may be of a mesh structure woven from filamentous materials, such as the double disk-shaped connected structure shown in FIGS. 1A and 1B. It is filled with blocking media to prevent blood from seeping into the interior of the occluder from around the body 100. For example, the body 100 may be woven from nickel-titanium alloy wire, iron wire, aluminum wire, polylactic acid or other materials, and filled with polytetrafluoroethylene, polyurethane, polyester or other materials as the blocking media. The body 100 includes two disk surfaces arranged opposite to each other, including a left heart disk surface 110 and a right heart disk surface 120. After the occluder is implanted in the interatrial septum, the left heart disk surface 110 faces the left atrium, and the right heart disk surface 120 faces the right atrium.

Different from common occluders, the body 100 has a through hole 130 in the axial direction inside, similar to an atrial shunt. However, the purposes of the atrial shunt and the occluder are completely different. The atrial shunt is used to be implanted into the interatrial septum of the patient's left and right atria to shunt and decompress the blood in the right atrium when pulmonary hypertension causes right heart failure.

According to the embodiments of the present disclosure, waist bundle braiding technology can be used to reduce the density of metal wires; special braided wires can be used to strengthen waist support and maintain the shape of the through hole; the tail end of the braid can be closed up and fixed by allowing the braid to be laterally eccentric and attached to a stainless steel nut sleeve 140 on the disk surface.

In addition to the above-mentioned body, the atrial septal defect occluder provided by the embodiments of the present disclosure further includes a blocking assembly, including an openable choke film or elastic body, wherein when the blocking assembly is in a closed state, the blocking assembly impedes liquid from flowing in the through hole 130 to achieve the blocking function. The blocking assembly in the embodiments of the present disclosure can weaken or even completely eliminate the blocking function if necessary, so as to realize the function of allowing a minimally invasive interventional device to pass or shunting According to embodiments of the present disclosure, the blocking assembly may be implemented in a variety of ways. Different implementations of the present disclosure will be introduced below with reference to multiple drawings.

According to embodiments of the present disclosure, the blocking assembly may be a choke film, which is of a thin film structure, for example, made of polytetrafluoroethylene, polyurethane, polyester, or other materials. In other embodiments of the present disclosure, the choke film may also be braided/woven, as shown in FIG. 2.

Figure 2:
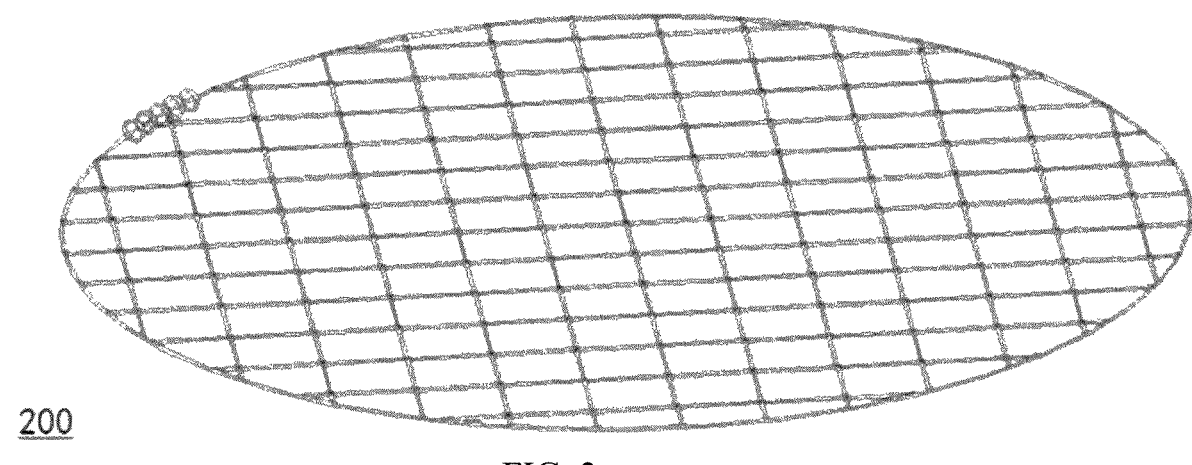
FIG. 2 is a schematic view of a choke film according to an embodiment of the present disclosure.

FIG. 2 is a schematic view of a choke film 200 according to an embodiment of the present disclosure.

As shown in FIG. 2, the choke film 200 may be woven from a filamentous material, and the pores in the surface are filled with blocking media. In some embodiments, the choke film 200 may be made of the same material and blocking media as the body 100. For example, the body 100 and the choke film 200 may be made and woven from at least one material of nickel-titanium alloy, iron, aluminum, polylactic acid, or other materials. The blocking media may be selected from polytetrafluoroethylene or polyurethane, etc., and coated on the surface of the braid.

According to an embodiment of the present disclosure, the area of the choke film is at least larger than the area of the through hole. Optionally, it may be larger than 1.5 or 2 times the area of the through hole to ensure that the through hole is covered.

According to an embodiment of the present disclosure, one end of the choke film is fixed to the body, and the other end remains open, that is, the choke film includes a fixed end and an open end. In some embodiments of the present disclosure, the choke film and the body are independently woven, and then one side is sewn to at least one side of the disk surfaces of the body by sewing. In other embodiments of the present disclosure, the choke film may be woven together with the body through the fixed end to form an integrally-formed structure.

In some embodiments of the present disclosure, the blocking assembly includes a choke film disposed on the left heart disk surface, the choke film is fixed to the left heart disk surface through the fixed end, and the choke film covers the through hole 130 in the closed state to achieve a flow blocking function. In the embodiments of the present disclosure, only the left heart disk surface is provided with a choke film, and the right heart disk surface is not provided with a choke film.

When the atrial septal defect occluder is placed at the atrial septal defect site, the choke film is located on the side of the left atrium. Since the pressure of the left atrium is greater than that of the right atrium, the pressure of the left atrium makes the choke film close to the left heart disk surface, to form a closed state, and the blood from the left atrium cannot enter the right atrium, thus achieving the blocking function of the interatrial septum. When it is necessary to shunt and decompress the atrial blood or perform interventional treatment on the left atrium, a minimally invasive interventional device (for example a cardiac catheter) can be used to enter from the right atrium and push the choke film to open, the blocking assembly switches to the open state to achieve communication between the left and right atria.

Figure 3A:
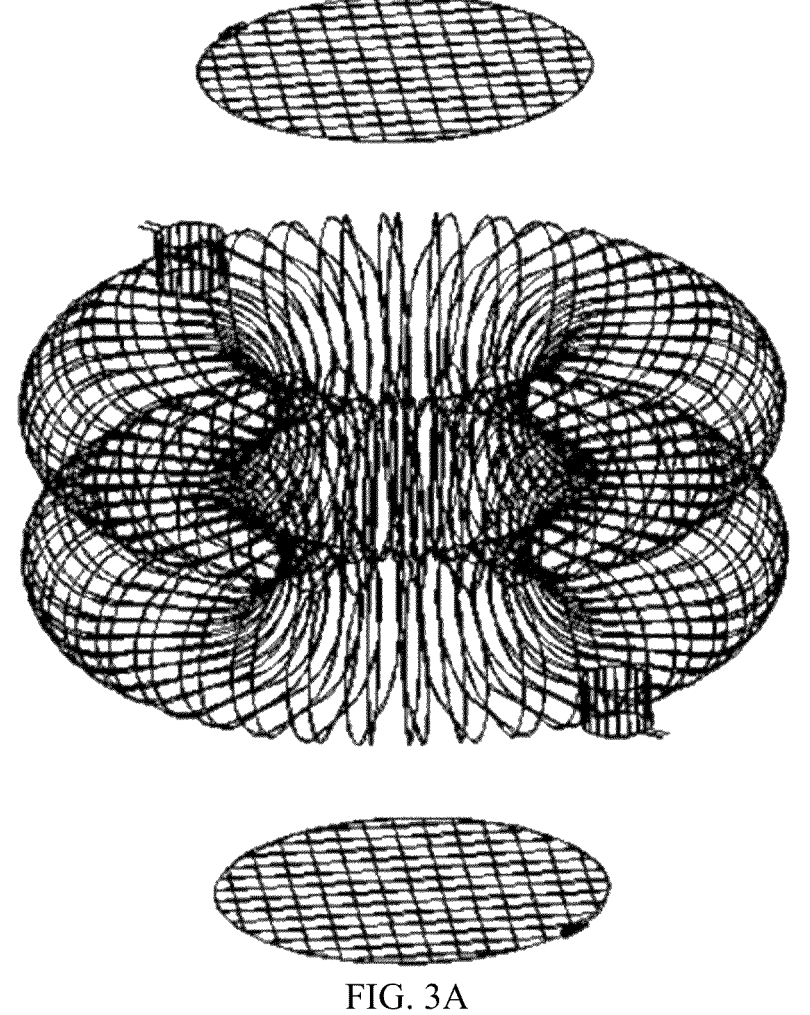
FIGS. 3A and 3B are schematic views of an atrial septal defect occluder according to an embodiment of the present disclosure.
Figure 3B:
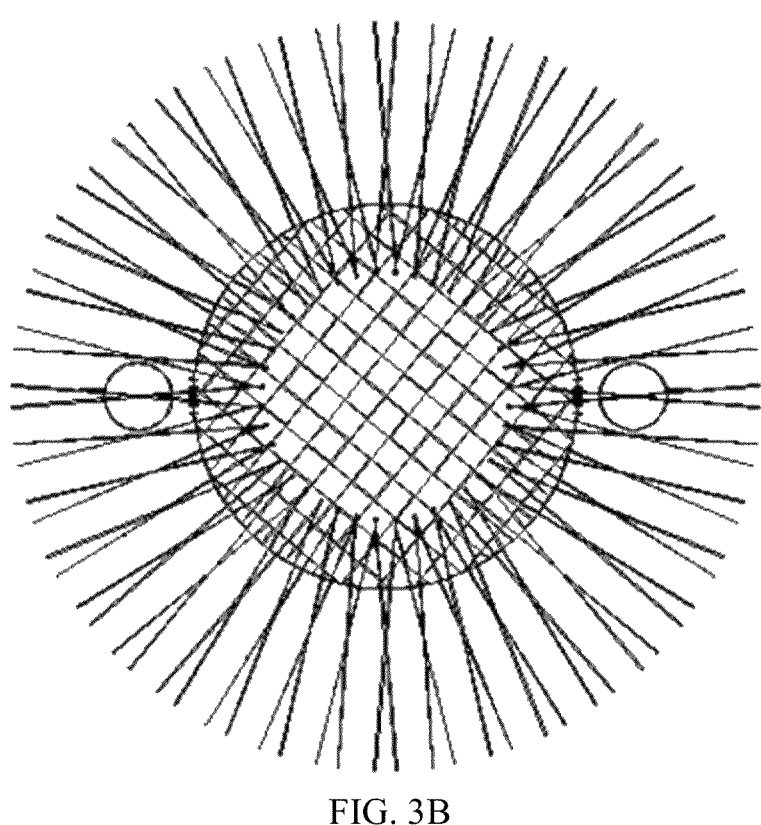

In other embodiments of the present disclosure, the blocking assembly includes two choke films respectively disposed on the two disk surfaces, each of the choke films comprises a fixed end and an open end, each of the choke films is fixed to one disk surface through the fixed end, and each of the choke films covers the through hole in the closed state, to achieve a flow-blocking function, as shown in FIGS. 3A and 3B. FIG. 3A shows a schematic assembly view of the atrial septal defect occluder, and FIG. 3B shows a top view of the atrial septal defect occluder.

According to the embodiments of the present disclosure, when the atrial septal defect occluder is placed at the atrial septal defect site, the blood on both sides is blocked by the choke films, thereby achieving the sealing of the left and right atria. When it is necessary to shunt and decompress atrial blood or perform interventional treatment on the left atrium, a minimally invasive interventional device (for example a cardiac catheter) can be used to open the choke film on the right heart disk surface from the side of the right atrium, enter the through hole, and push to open the choke film on the left heart disk surface, so that the left and right atria are communicated with each other, in this case, the blocking assembly switches to the open state. According to the technical solutions of the embodiments of the present disclosure, the choke films are provided on both sides, after implantation in the body, the blood on the right atrium side will not enter the through hole, thus avoiding the formation of thrombus in the through hole.

According to an embodiment of the present disclosure, a pulling wire is provided on the open end of the choke film of the right heart disk surface, so that the choke film on the right heart disk surface can be easily opened by pulling the pulling wire, and then the minimally invasive interventional device enters the through hole, pushes to open the choke film on the left heart disk surface to realize the communication between the left and right atria.

In other embodiments of the present disclosure, the blocking assembly includes a choke film disposed on the left heart disk surface, the choke film is peripherally fixed to the left heart disk surface and covers the through hole, the choke film is provided with an opening, and the opening and the through hole have no overlapping portion in the axial direction of the occluder, i.e., the projections of the opening and the through hole in the axial direction of the occluder do not overlap with each other.

According to the technical solutions of the embodiments of the present disclosure, when the pressure of the right atrium is higher than that of the left atrium, the blood will push up the choke film on the left heart disk surface, so that the choke film is no longer tightly attached to the left heart disk surface, leaving a certain space, in this case, the blocking assembly is switched to the open state, so that the blood in the right atrium can flow to the left atrium through the opening, thereby reducing the pressure in the right atrium. In addition, when the minimally invasive device needs to enter the left atrium, the choke film on the left heart disk surface can be slightly lifted, and the minimally invasive device can pass through the opening.

The choke film in this embodiment is preferably of a thin film structure, for example, made of polytetrafluoroethylene, polyurethane, polyester or other materials, rather than having a woven structure, in this way, it can better fit the left heart disk surface.

It can be understood that, in the embodiments where a choke film with an opening is disposed on the left heart disk surface, a choke film may still be disposed on the right heart disk surface to prevent blood from the right atrium from entering the through hole and avoid the formation of thrombus. The choke film on the right heart disk surface may, for example, include a fixed end and an open end as described above, it is fixed to the right heart disk surface through the fixed end and covers the through hole in the closed state.

Figure 4A:
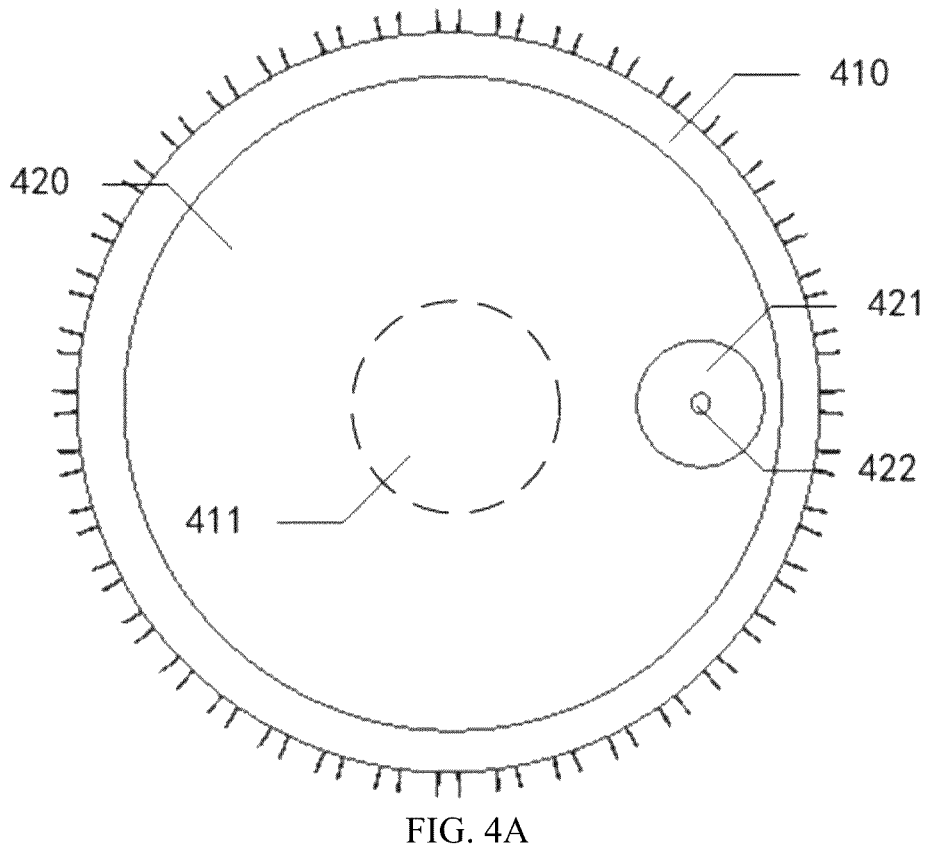
FIGS. 4A and 4B are schematic views of an atrial septal defect occluder according to another embodiment of the present disclosure.
Figure 4B:
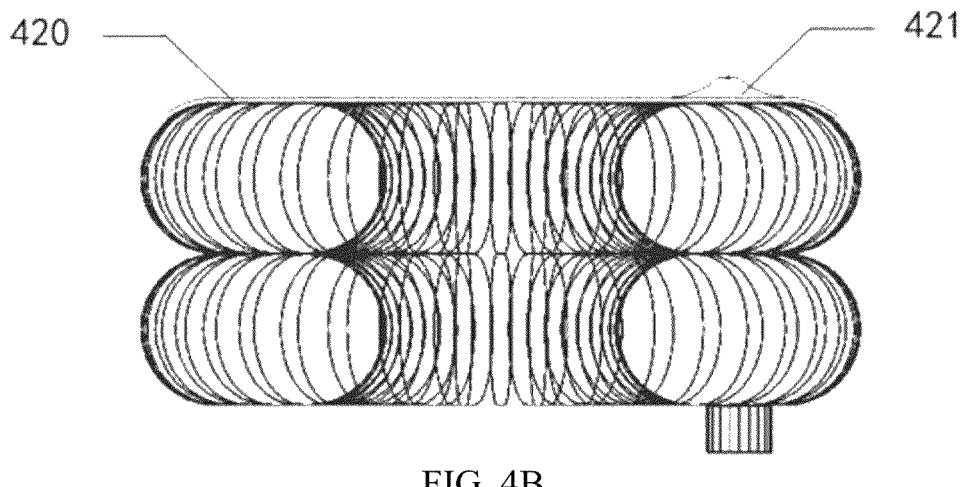

According to an embodiment of the present disclosure, the choke film disposed on the left heart disk surface may have a raised portion, and the opening is provided at the top of the raised portion, as shown in FIGS. 4A and 4B. FIG. 4A shows a top view of the atrial septal defect occluder according to the embodiment of the present disclosure, and FIG. 4B shows a side view of the atrial septal defect occluder according to the embodiment of the present disclosure.

As shown in FIGS. 4A and 4B, on one side of the left heart disk surface of the body 410, the choke film 420 has at least one raised portion 421, and an opening 422 is provided at the top of the raised portion 421. In FIG. 4A, the dotted line shows the location of the through hole 411. In the embodiment of the present disclosure, in the axial direction of the occluder, the raised portion 421 has no overlapping portion with the through hole 411, so that the choke film can still block the through hole 411.

In addition to using the choke film, the blocking assembly of the embodiments of the present disclosure may be an elastic body filled in the through hole, a channel is provided inside the elastic body, and the channel is configured to be sealed by an elasticity of the elastic body.

Figure 5A:
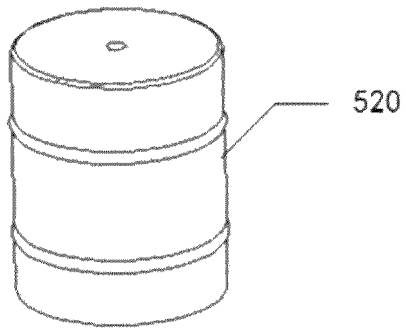
FIGS. 5A to 5E are schematic views of an atrial septal defect occluder according to yet another embodiment of the present disclosure.
Figure 5A:
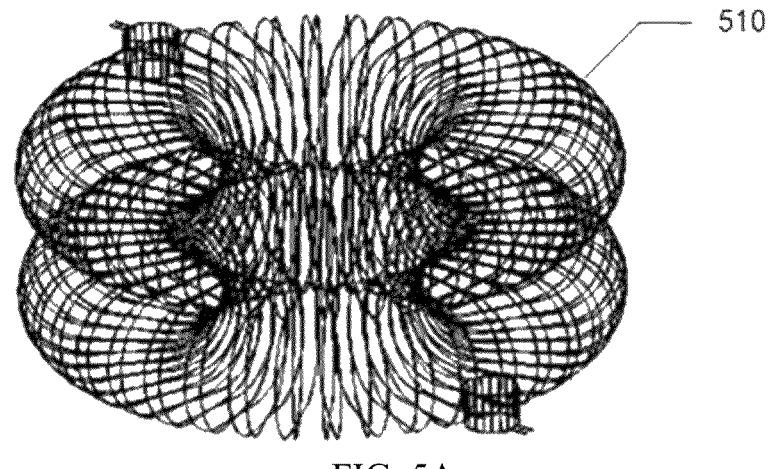
Figure 5B:
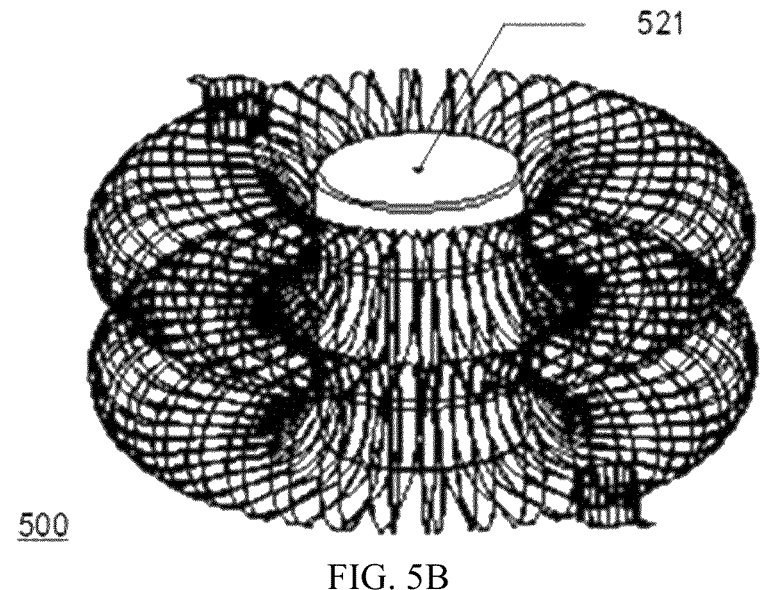
Figure 5C:
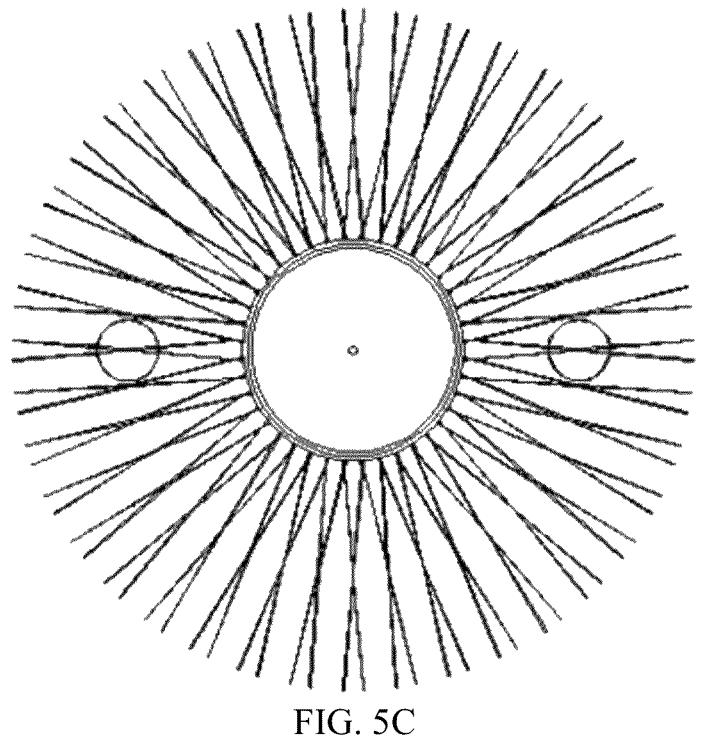
Figure 5D:
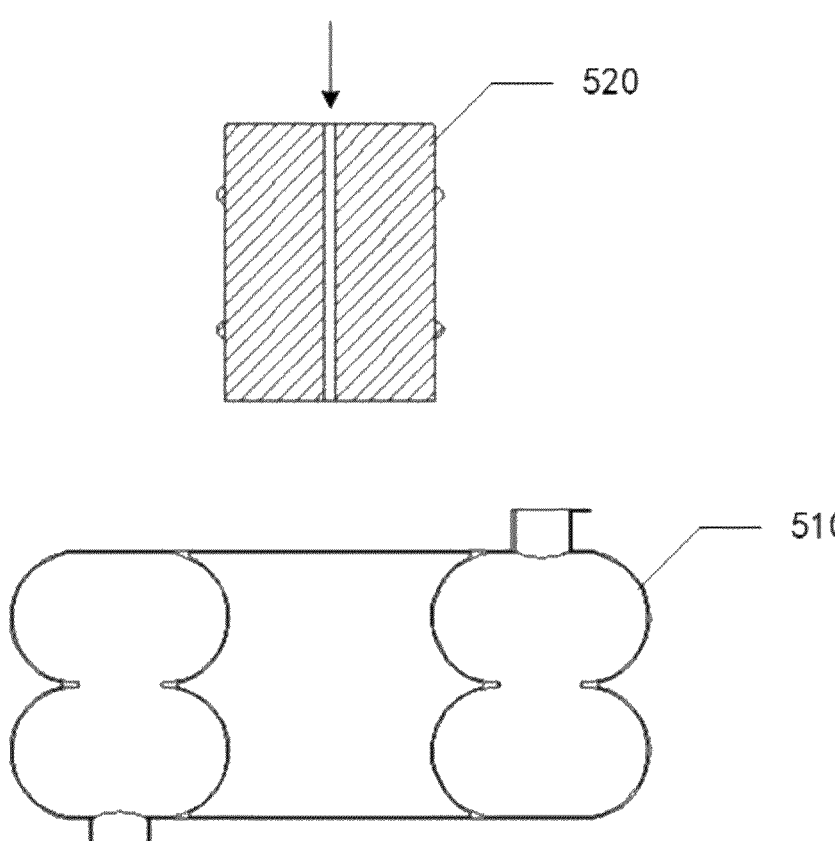
Figure 5E:
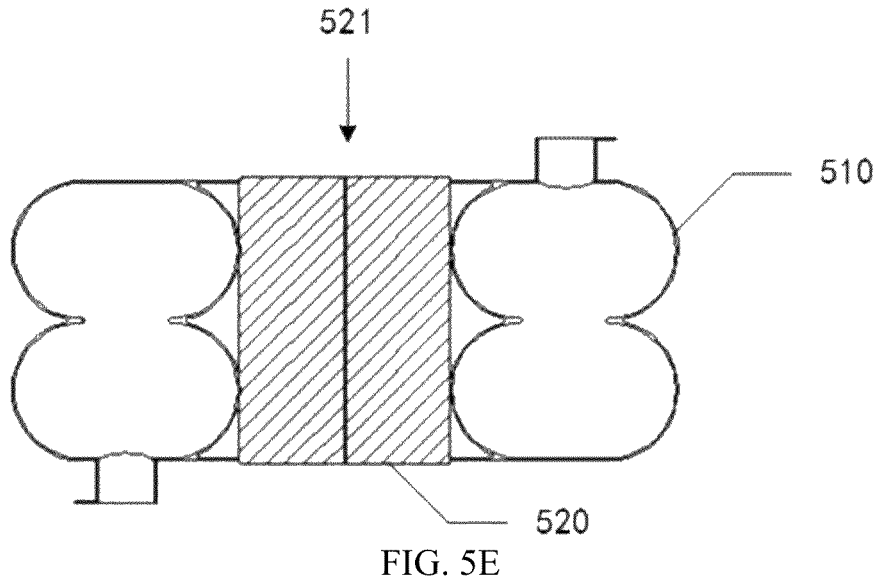

FIGS. 5A to 5E show schematic views of an atrial septal defect occluder according to another embodiment of the present disclosure. FIG. 5A is a schematic assembly view of the atrial septal defect occluder, FIG. 5B is a perspective view of the atrial septal defect occluder, FIG. 5C is a top view of the atrial septal defect occluder, FIG. 5D and FIG. 5E are schematic side-view diagram of the atrial septal defect occluder.

As shown in FIGS. 5A to 5E, the atrial septal defect occluder 500 includes a body 510 and a blocking assembly 520. For the body 510, reference can be made to the description of the body 100 above, it will not be described again here. The blocking assembly 520 is an elastic body and is accommodated in the through hole inside the body. The elastic body 520 may be, for example, a polyurethane elastic body or polytetrafluoroethylene elastic body.

According to an embodiment of the present disclosure, the elastic body 520 is provided with a channel 521 inside. Normally, the channel 521 remains closed under the action of elasticity, and liquid does not pass through the channel 521, that is, the blocking assembly is in a closed state; when interventional treatment of the left atrium is required, a minimally invasive interventional device (for example, a cardiac catheter) enters from the right atrium, squeezes out the channel 521 and passes through it, and enters the left atrium, in this case, the blocking assembly is switched to the open state, and then the treatment equipment such as the guide wire is introduced from the cardiac catheter into the left atrium for treatment.

In the technical solutions provided by the embodiments of the present disclosure, since the elastic body fills the through hole, blood will not enter the through hole, and the occurrence of thrombus can be avoided.

According to an embodiment of the present disclosure, a developing line is provided in the channel of the elastic body to facilitate finding the location of the channel 521.

Compared with traditional occluders that only have a blocking function, the atrial septal defect occluder in the embodiments of the present disclosure can not only achieve atrial septal blocking, but can also open when necessary, thereby avoiding the problem of causing harm to the patient by repeatedly punching holes in the patient's interatrial septum during multiple treatments.

The above description only refers to optional embodiments of the present disclosure and an illustration of the technical principles used. It should be understood by those skilled in the art that the scope of the invention involved in the present disclosure is not limited to technical solutions formed by a specific combination of the above technical features, but should also cover other technical solutions formed by any combination of the above technical features or equivalent features without departing from the concept of the invention, for example, the technical solutions formed by replacing the above features with technical features disclosed in present disclosure (but not limited to) with similar functions.

What is claimed is:

1. An atrial septal defect occluder, comprising:
   a body, comprising two disk surfaces arranged opposite to each other and provided with a through hole along an axial direction of the body, wherein the two disk surfaces comprise a left heart disk surface and a right heart disk surface; and
   a blocking mechanism, comprising an openable choke film, the blocking mechanism being in contact with the body,
   wherein when the blocking mechanism is in a closed state, the blocking mechanism impedes liquid from flowing in the through hole, and when the blocking mechanism is in an open state, a blocking effect is weakened or even eliminated, thus allowing a minimally invasive interventional device to pass through the occluder by means of the through hole;
   wherein the blocking mechanism comprises a choke film disposed on the left heart disk surface, wherein a portion of a periphery of the choke film is fixed to the left heart disk surface and wherein the choke film is configured such that when pressure of a right atrium is higher than that of a left atrium, the choke film is no longer tightly attached to the left heart disk surface, creating a space so that blood in the right atrium can flow to the left atrium through the opening, thereby reducing pressure in the right atrium; and further wherein, when the minimally invasive device needs to enter the left atrium, the choke film on the left heart disk surface can be slightly lifted, and the minimally invasive device can pass through the opening;
   wherein the body and the choke film are constructed using a braided nickel-titanium alloy wire;
   wherein a tail end of the braided wire is laterally eccentric relative to the through hole and is attached to a stainless steel nut sleeve on one of the disk surfaces, wherein the stainless steel nut sleeve is configured to strengthen, support, and help maintain the shape of the through hole;

wherein the braided wire forms a mesh structure;

wherein the choke films comprises pores on a surface of the choke film, the pores being filled with polytetrafluoroethylene or polyurethane.

* * * * *